United States Patent [19]

Perchorowicz et al.

[11] Patent Number: 5,147,792
[45] Date of Patent: Sep. 15, 1992

[54] METHOD OF SHIFTING THE FATTY ACID DISTRIBUTION IN PLASTIDS TOWARDS SHORTER-CHAINED SPECIES BY USING THIOESTERASE II AND ACYL CARRIER PROTEIN

[75] Inventors: John T. Perchorowicz, Tucson, Ariz.; Andree L. Genez, Tuscon; Vic C. Knauf, both of Davis, Calif.

[73] Assignee: Calgene, Inc., Davis, Calif.

[21] Appl. No.: 279,047

[22] Filed: Nov. 29, 1988

Related U.S. Application Data

[63] Continuation-in-part of Ser. No. 916,885, Oct. 9, 1986, abandoned.

[51] Int. Cl.$^5$ ............................................. C12P 7/64
[52] U.S. Cl. ................................... 435/134; 435/135
[58] Field of Search ............................................ 435/134

[56] References Cited

PUBLICATIONS

Bach, A. C. & Babayan, V. K., Am. J. Clin. Nutr. (1982) 36:950–962.
Cao, Y & Huang, A. H., Plant Physiol. (1987) 84:762–765.
Della-Cioppa, G., et al., Plant Physiol. (1987) 84:965–968.
Smith, S.,Biochem. J. (1983) 212:155–159.
Smith, S., et al., JNCL (1984) 73:323–329.
Knauf, V., TIBTECH (1987) 5:40–47.
Libertini, L. J. & Smith, S., Arch. Biochem. & Biophys. (1979) 192:47–60.
Libertini, L. J. & Smith, S., J. Biol Chem., (1978) 253:1393–1401.
Smith, S. & Libertini, L. J., Arch. Biochem. & Biophys. (1979) 196:88–92.
Smith, S., J. Dairy Sci. (1980) 63:337–352.
Bayley, et al., Bio/Tech (1988) 6:1219–1221.
Smith, et al., Biochem. Soc. Trans. (1986) 14:583–584.
Naggert, et al., Biochem. J. (1987) 243:597–601.
Randhawa, et al., Biochem. (1987) 26:1365–1373.
Knudsen and Dils, Biochem. J. (1976),160:683–691.
Ohlrogge, et al., Proc. Natl. Acad. Sci. USA (1979) 76:1194–1198.
Smith, Methods In Enzymology (1981) 71:188–200.
Rogers & Kolattukudy, Anal. Biochem. (1984) 137:444–448.
Stumpf, Biochemistry of Plants (1980) 4:177–204.
Boyle, et al., Plant Physiol. (1986) 81:817–822.
Jensen and Bassham, Proc. Natl. Acad. Sci. USA (1966) 56:1095–1101.
Shimakata and Stumpf, "The Procaryotic Nature of the Fatty Acid Synthetase of Developing *Carthamus tinctorius* L. (Safflower) Seeds", Arch. of Biochem. Biophys. (1982) 217:144–154.
Shimakata and Stumpf, "Fatty Acid Synthetase of *Spinacia oleracea* Leaves", Plant Physiol. (1982) 69:1257–1262.
Kuo and Ohlrogge, "The Primary Structure of Spinach Acyl Carrier Protein", Arch. of Biochem. Biophys. (1984) 234:290–296.
Simoni et al., "Fat Metabolism in Higher Plants XXXI. Purification and Properties of Plant and Bacterial Acyl Carrier Proteins", J. Biol. Chem. (1967) 242:573–581.
Hoj and Svendsen, "Barley Acyl Carrier Protein: Its Amino Acid Sequence and Assay Using Purified Malonyl–CoA:ACP Transacylase", Carlsberg. Res. Comun. (1983) 48:285–305.
*Enzyme Nomenclature* (1984) Academic Press p. 574.
Hoj, P. B. & I. B. Svendsen, Barley Acyl Carrier Protein Carlsberg Res. Comm. 48(285–305) 1983.
Simoni, R. D. et al., Fat Metabolism in Higher Plants J.B.C. 242:573–581 (1967).
Knudsen, Medium Chain Fatty Acyl Thioesterase in *Methods in Enzymology* vol. 71 (1981) pp. 200–229.

*Primary Examiner*—Douglas W. Robinson
*Assistant Examiner*—S. Saucier

[57] ABSTRACT

Methods and compositions are provided for producing plant fatty acids employing mixtures of enzymes, where the composition is modified by reducing or enhancing the relative proportion of one or more enzymes or adding an exogenous enzyme. Particularly, compositions can be produced having enhanced amounts of fatty acids containing 14 or fewer carbon atoms using thioesterase II or acyl carrier protein.

9 Claims, 1 Drawing Sheet

METHOD OF SHIFTING THE FATTY ACID DISTRIBUTION IN PLASTIDS TOWARDS SHORTER-CHAINED SPECIES BY USING THIOESTERASE II AND ACYL CARRIER PROTEIN

This application is a continuation-in-part of U.S. application Ser. No. 916,885, filed on Oct. 9, 1986, now abandoned. This disclosure of Ser. No. 916,885 is hereby incorporated reference.

BACKGROUND OF THE INVENTION

1. Field of the Invention

This invention is related to control of the types and amounts of fatty acids present in plant tissues and is particularly related to methods for increasing the percentage of fatty acids containing sixteen or fewer carbon atoms, preferably 14 or fewer.

2. Description of the Background

Fatty acids are ubiquitous in living forms, providing glycerides essential to membrane formation, as precursors to a wide variety of products, and as stored energy. The most abundant fatty acids tend to be the longer chain fatty acids, such as palmitate (C16:0) and stearate (C18:0). These higher fatty acids lack the many desirable properties of the shorter chain fatty acids in the range of about 8 to 12 carbon atoms, and even C14 carbon chain, which have lower melting points and can find use in a variety of applications in food, specialty oils, paints, lubricants, detergents, and the like. Fatty acids containing 8 to 14 carbon atoms are considered "medium chain fatty acids."

For the most part, animal fats tend to be longer chains (e.g., 16:0, 18:0). Traditionally, the commercial source of oils high in medium chain fatty acids are coconut oil and palm kernel oil. Both of these products are grown only in tropical climates and are subject to wide annual variations in cost and availability. Alternative sources of medium chain fatty acids are needed.

The fatty acids are synthesized in plants in the chloroplast, proplastid, or related organelles. It is therefore of interest to be able to selectively modify the chloroplast fatty acid synthesizing system to change the fatty acid composition and distribution to produce fatty acid compositions which are different from the fatty acid composition normally produced by the particular species.

DESCRIPTION OF RELEVANT LITERATURE

Stumpf *Biochemistry of Plants* (1980) 4:177-204 (Academic Press) describes the biosynthesis of fatty acids in plants, localizing that synthesis in chloroplasts and/or protoplasts. Boyle, et al., *Plant Physiol.* (1986) 81:817-822 report that leucoplasts (also known as "proplastids") have a protein import mechanism similar to that of chloroplasts. Jensen and Bassham, *Proc. Natl. Acad. Sci. USA* (1966) 56:1095-1101 describe the isolation of photosynthetically competent chloroplasts from spinach leaves. Ohlrogge, et al., *Proc. Natl. Acad. Sci. USA* (1979) 76:1194-1198 describe a fatty acid synthesis reaction mixture suitable for use with spinach chloroplasts. Badami and Patil (1981) describe some of the potential diversity found in the fatty acid contents of various plant tissues.

Smith, *Methods in Enzymology* (1981) 71:188-200 describes the purification of a medium-chain fatty acyl-S-4'-phosphopantetheine—fatty acid synthase thioester hydrolase (a thioesterase II) from rat ("rte II"). A thioesterase II gene has also been purified from the uropygial gland of the mallard: Rogers & Kolattukudy, *Anal. Biochem.* (1984) 137: 444-448. The rat thioesterase II cDNA sequence and a discussion of homology between the rat and mallard proteins is found in Naggert, et al., *Biochem J.* (1987) 243:597-601. See also, Randhawa, et al., *Biochem* (1987) 26:1365-1373. Purified thioesterase II protein has also been obtained from mammary glands of rabbit, Knudsen and Dils, *Biochem. J* (1976) 160:683-691. Unpublished work by S. Smith regarding the purification of thioesterase II enzymes obtained from mammary glands of the mouse has been reported, Smith, et al., *Biochem. Soc. Trans.* (1986) 14: 583-584. Fatty acid synthetases purified from ruminant glands (such as goat, cow and sheep) had the ability to hydrolyze medium chain acylthioesters, Smith, S., *J. Dairy Sci.* (1980) 63:337-352. Bayley, et al., *Bio/Tech* (1988) 6: 1219-1221, reports production of medium chain triacylglycerides in mouse fibroblasts transfected with rat thioesterase II.

SUMMARY OF THE INVENTION

A method is provided for changing the fatty acid composition produced by plastids, such as chloroplasts, proplastids or the like, from a composition having a given proportion of fatty acids to a composition having a lower proportion of higher fatty acids. By higher fatty acids is meant fatty acids having more than sixteen, preferably more than fourteen, carbon atoms. The method comprises combining the fatty-acid-producing components of a plastid, such as chloroplasts, proplastids, or the like with a protein, which can be obtained from an entirely different organism, that divert a metabolite in the fatty acid synthesis pathway and results in the production of a lower fatty acid. Sufficient metabolites in the fatty acid pathway must be present in order for fatty acids to be produced, the metabolites being malonyl-CoA and either acetyl-CoA or a metabolite subsequent to malonyl-CoA in the metabolic pathway. The reaction is allowed to proceed to produce a modified fatty acid composition which can then be separated, if desired from other components of the chloroplast or other plastid.

The present invention also comprises a method for selecting the additive that is to be combined with the fatty-acid-producing components of the chloroplast system. This method is carried out in vitro utilizing the fatty-acid-producing components of the chloroplast, typically from isolated and broken chloroplasts, to which a protein being tested is added.

The present invention is also directed to plant seeds produced by a plant grown in accordance with the method of this invention. Seed harvested from a plant having in its genome a heterologous construct comprising, in the order of transcription, a transcription initiation region (preferably a seed-specific transcription initiation region), in open reading frame, a plastid-translocating sequence joined to a sequence encoding a protein having thioesterase II activity, and a termination region will be enriched in medium chain fatty acids. In another embodiment, this invention comprises the oil recovered from the crushing of such seed.

DESCRIPTION OF THE SPECIFIC EMBODIMENTS

Figure 1:
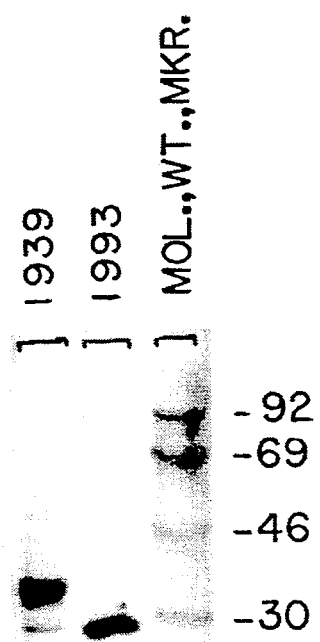
FIG. 1 is a picture of a gel showing uptake of the protein encoded by pCGN1993 by tobacco chloroplasts.

Modifications of plant oil compositions are provided by bringing together the fatty-acid-synthesizing components of plastids, i.e., chloroplasts, proplastids, or related organelles, in conjunction with an elevated amount of a protein that is capable of diverting a component of the synthesis system, for example, thioesterase II. Also, by providing appropriate substrates for the modified chloroplast composition, one can test for the enhancement of the amount of the less abundant, lower molecular weight (shorter chain) fatty acids.

The modified plant oil compositions may be obtained in vitro or in vivo by employing chloroplast preparations in combination with exogenously added proteins or by providing for expression of genes encoding such identified proteins in plant cells which transport the proteins from the cytoplasm to the plastid, i.e., chloroplast, proplastid, or related organelle. The plant cells may be in culture or in a plant part. Particularly, where the added genes are present in the plant cell nucleus, expression will be controlled by promoters which preferentially initiate transcription in the seed.

The components of the fatty-acid-synthesizing compositions that are used in the practice of this invention may be obtained from any plant source but may vary depending upon whether the fatty acids are to be produced in vitro or in vivo. In vitro preparations will be chosen for their convenience, reproducibility, easy manipulation, stability and the like. Sources of the chloroplast systems and systems of related organelles include but are not limited to spinach, tobacco, cuphea and oil palm. For in vivo production of shorter chain fatty acids, plants will preferably be chosen which provide for high oil content in the seed. These plants include but are not limited to *Brassica,* cuphea, soybean, sunflower, safflower, cotton, peanut, tobacco, flax, linseed, castor, etc. Especially preferred are the seeds of *Brassica napus.* Seeds of such plants are also often known as oilseeds.

In preparing the fatty-acid-synthesizing compositions for use in vitro, chloroplasts may be isolated by chilling leaves and, while maintaining the leaves chilled, cutting and mincing the leaves and covering the pieces with a buffered medium. The leaves, in the presence of the aforementioned medium, may be minced by grinding or by any other technique which will substantially disrupt the plant cells and release the organelles. The resulting macerated leaves are filtered and the organelles isolated and concentrated, commonly by centrifugation or other convenient means. The resulting concentrated organelles, primarily chloroplasts, are osmotically lysed and added to the fatty-acid-synthesis reaction mixture.

Alternatively, fatty-acid-synthesizing systems may be obtained from embryonic plant tissue. The tissue may b disrupted in a buffered medium by grinding or by any other technique which will substantially disrupt the cells and release the fatty-acid-synthesizing enzymes. The resulting disrupted embryonic tissue is commonly processed by centrifugation to yield a solution containing the fatty acid synthesizing enzymes.

The fatty-acid-synthesis reaction mixture is made in an appropriate buffered medium to which is added one or more electron transfer substances, typically NADH and NADPH to provide concentrations of 0.3 to 1.2 mM and 0.3 to 0.9 mM, respectively. Also added is an energy source, typically ATP, to provide a concentration in the range of 1 to 3mM. In addition, the substrates malonyl-CoA and either acetyl-CoA or a metabolite subsequent to malonyl-CoA in the fatty acid pathway will be added in amounts of from about 4 to 12μM. Conveniently, the various components are brought together in an appropriate medium, such as water or an aqueous buffer at a physiologically acceptable pH, and may then be added directly to the chloroplast suspension or enzyme solution.

One or more proteinaceous additives, e.g. acyl carrier protein (ACP), acetyl transacylase (ATA), or rat thioesterase II (rteII) or enzymes performing analogous functions, are added. Of special interest are rteII or enzymes performing analogous functions. Thioesterase II is present in the mammary glands of lactating rats, rabbits, mice, goat, cow and sheep, for example, and the uropygiol gland of mallard ducks. Any source of thioesterase II is acceptable. A partial, modified, or mutated amino acid sequence, or other analogous sequence may be used as long as thioesterase II activity is present. Thioesterase II is characterized by its ability to hydrolyze acyl-CoA thioesters. The enzyme acts by cleaving the ACP moiety from elongating fatty acid chains and thereby preventing further elongation by the fatty acid system. The enzyme specificity results in an increased level of medium chain fatty acids. The acyl-ACP thioesterase II enzyme found in the mammary glands of lactating rats, for example, generates medium chain fatty acids by removing ACP from acyl chains at about 10, 12 and 14 carbons in length which results in a milk rich in these medium chain fatty acids.

The proteins may be added to either the fatty-acid-synthesis system or to the additive in the appropriate concentration. Generally, the amount of each additive protein will vary depending upon the particular nature of the protein, e.g., source, activity, desired change in the fatty acid composition, presence or absence of other added proteins, and source of the fatty-acid-synthesis system. Thus, for the most part, the concentration of these proteins will be determined empirically. However, one may usefully begin with a protein concentration of from about 0.01 to 0.3 mg protein/ml for materials that are not enzymes (such as carrier proteins) and activities of 1 to 20 mMol/min/ml of activity for enzymes. These concentrations can readily be adjusted up or down depending on whether too low (including zero) or too high an activity, respectively, is determined.

The proteinaceous component to be used as an additive is normally selected with at least some knowledge of its properties. Typically, a proteinaceous additive is selected that will utilize an intermediate in the chloroplast fatty-acid-synthesizing system as a substrate and direct that intermediate to the formation of a desired short-chain fatty acid. Such proteins are sometimes referred to as termination factors in that they terminate the processes that lead to longer chain formation (i.e., they terminate chain elongation). The termination factor can be complementary to an enzyme, carrier protein, or the like of the plant system that results naturally in the production of a short-chain fatty acid or it may be supplementary to the plant system (i.e., it may provide a function that is not part of or equivalent to any part of the plant fatty-acid-synthesis system, such as providing a pathway to a short-chain fatty acid that is not a natural product of the synthesis system). Complementary here means either an identical function (e.g., adding a greater than natural amount of a component already present), an equivalent function (e.g., adding a component, such as an esterase that carries out the same function with the same substrate but which is obtained from a heterologous source), or a similar function (e.g., adding a carrier protein from a different system having different characteristics but being capable of accomplishing the result of transporting a fatty acid of the type being synthesized). For example, thioesterases obtained from rats and acyl carrier proteins from bacteria (such as *E. coli*) can be utilized even though they are not normally present in plants since they are capable of catalyzing reactions of substrates, such as decanoyl-CoA, that are precursors of long-chain fatty acids and removing them from the normal synthetic pathway.

The broken chloroplast composition will usually have about the following initial concentrations: broken chloroplasts equivalent to 1 mg chlorophyll/ml of reaction; NADH 0.4 mM; NADPH 0.3 mM, buffer 100 mM (useful buffers include MES ((2-N-morpholino) ethanesulfonic acid), MOPS (3-(N-morpholino) propanesulfonic acid), or TES (2-((tris-(hydroxymethyl)methyl-)amino) ethanesulfonic acid) at a concentration in the range of 50 to 150mM and a pH in the range of 6 to 8); ATP 1 mM; trace metals 0.5mM total, particularly magnesium and manganese chloride; chelating agent 0.5mM, particularly EDTA; and acetyl-CoA and malonyl-CoA 4mM. The embryonic-tissue-derived fatty acid system will usually contain similar initial concentrations of components except that protein concentrations will be about 0.5-1.0mg/ml of reaction mixture place of chloroplasts and no chelating agent is present.

The in vitro preparation of fatty acids may be carried out at ambient temperatures, with the temperature usually about 30° C. Mild agitation may be employed, such as stirring, shaking, or the like. The time for the reaction will vary widely, depending upon whether the fatty acid synthesizing system is being used as a preparative system or an assay and upon the nature of the system employed. Usually, the reaction will be terminated when the yield of the desired fatty acid has reached a plateau, which may be dependent upon the malonyl-CoA or acetyl-CoA being depleted, one or more of the active components having become inactive, or the like.

At the completion of the fatty acid synthesis, which production may be terminated by addition of an extraction solvent, the fatty acid profile may be determined. The reaction mixture is typically extracted with an appropriate hydrophobic extraction solvent, e.g., methanol/chloroform. With methanolic chloroform, an aqueous KCl solution is added, the resulting layers separated, and the lower solvent layer evaporated at ice temperature. The residue is dissolved in methanol and commonly saponified at 80° C. for 20 minutes to ensure the complete hydrolysis of the esters. The fatty acids can be derivatized with an appropriate derivatizing agent to form an alkyl or aralkyl ester, e.g., p-bromophenacyl ester, in high yield in order to facilitate analysis. Conveniently, elevated temperature, e.g., 60° to 90° C., and a polar organic solvent, e.g., acetonitrile, may be employed to ensure the completion of the reaction. The resulting derivatized fatty acid esters may then be separated on a high-performance-liquid-chromatography column with an aqueous acetonitrile solvent (e.g., 20% water), and the individual fatty acid fraction determined by conventional ways, e.g., weighing, sepctrophotometrically or by detection of incorporated radiolabel.

The procedures described above can be utilized either as a preparative technique or, prior to demonstration of a positive result for any given proteinaceous additive to be tested, as an assay. Based on experience with the assay, one can introduce one or more genes into plant cells for expression of the gene in vivo, whereby the system for producing fatty acids in, for example, the chloroplasts or proplastids may be modified. This technique may involve the addition of one or more copies of the gene coding for the protein additive (e.g., the enzyme rteII or enzymes catalyzing analogous functions), by themselves or in conjunction with other genes which may enhance the concentration of one or more of the components involved in the production of fatty acids in chloroplasts or related organelles.

Once a desired protein additive is identified, a DNA sequence corresponding thereto may be achieved in a number of ways. For example, if the protein additive has been purified and partially sequenced, a oligonucleotide probe may be designed for screening a cDNA library or a genomic library to identify candidates/DNA sequences which encode this protein. In addition, DNA sequence information derived from a targeted and positively identified cDNA sequence can be used to derive an oligonucleotide probe with which a genomic library can be screened to identify a genomic DNA sequence. Alternatively, the desired protein can be used to generate antibodies which can be used to screen an expression library for a clone expressing an antibody cross-reactive antigen. An expression library is derived by cloning a cDNA library into a host system which will transcribe and translate the DNA sequence protein. In any event, the method of preparing a DNA sequence to encode the protein additive is not critical to this invention, the above examples are provided for illustration purposes only. Importantly, however, the DNA sequence must encode a biologically active protein.

In order to increase the localized concentration in the chloroplast, proplastid, or related organelle of the particular proteins of interest, it is helpful to introduce the genes into the plant cell with a portion (preferably the 5'-terminus) of a gene coding for an appropriate transit peptide for translocating the protein of interest to the plastid, such as the chloroplast or proplastid. Preferably the 5'-terminus portion of the gene encoding for an appropriate transit peptide includes a transit peptide sequence and the first few amino acids of mature protein sequence. A transit peptide sequence is involved in binding of the precursor protein to the plastid envelope. During the process of entry into the plastid, the transit peptide is cleaved from the precursor protein and "mature" protein is released into the organelle. (The protein is deemed "mature" even if additional processing is required for functionality.) Thus, a plastid-translocating sequence may include the transit peptide and first few amino acids of mature protein sequence or may only require the transit peptide sequence, for example.

Transit peptides which are known and have been characterized include those transit peptides associated with the genes encoding the small subunit to ribulose bisphosphate carboxylase, the light harvesting chlorophyll a/b protein, and pyruvate orthophosphate dikinase. Other proteins which are known to be transcribed in the nucleus, translated in the cytoplasm, and translocated to the chloroplast include ACP and some heat-shock proteins. The particular choice of transit peptide will be dependent upon availability, efficiency of translocation, ease of use of the transit peptide in the construction, effect on cellular growth, and the like. A preferred sequence for translocation, particularly to the proplastid, is an ACP transit peptide joined to the first 11 amino acids of mature ACP (Rose, et al., *Nuc. Acids Res.*, 15:7197 (1987).

The first few amino acids of mature protein sequence includes approximately the first 10-30 amino acid residues, also known as approximately 10-30 amino acids of N-terminal mature polypeptide sequence. When the protein of interest translocated to the plastid includes the first few amino acids of the N-terminal mature protein sequence, it should be noted that the protein released into the organelle will contain additional amino acids at the N-terminus, which may affect the enzymatic activity of the protein of interest.

As noted above, the gene encoding the protein to be translocated to the chloroplast may be a plant, animal or microbial gene. The DNA sequence may be synthetically prepared. The gene may be wild-type or mutant, either naturally occurring or induced in vitro. Thus, the various proteins may be modified to optimize their effect on the fatty acid composition and/or to facilitate ease of joining with the translocation sequence. Sources for genes for ACP, ATA, rteII or enzymes catalyzing analogous function include bacteria; yeast; mammals, such as rats, mice, rabbits, elephants and primates; other vertebrates, such as birds; other animals; and plants, either the same plant as the plant being transformed or a plant of the same family or a different family.

Once the gene encoding the protein and the sequence encoding the transit peptide are defined, the two DNA sequences may be joined in a variety of ways. Where convenient restriction sites exist both in relation to the transit peptide sequence and the gene sequence, so as to bring the two sequences into proper reading frame, the two sequences may be joined by ligation to provide for the modified gene with the transit peptide. Where such a restriction site does not exist, various techniques may be employed, such as cutting at different sites internal to the coding sequences and employing a linker which recreates the necessary nucleotides and provides for an open reading frame extending from the transit peptide through the structural gene. Alternatively, one can use the in vitro mutagenesis, primer repair, or the like, to modify one or more nucleotides so as to provide for an appropriate site for joining the transit peptide and/or the structural gene sequences, so that the two sequences may be joined in proper reading frame. The particular manner in which the joining of the two sequences is achieved is not critical to the subject invention.

A useful aspect is to employ a transcription initiation region which is subject to cellular differentiation control. In particular, seed-specific transcription initiation regions are preferred, especially those which are active in embryos during seed maturation. Thus, the transcription initiation region will be associated with genes which are expressed during seed formation, such as storage protein genes, including the glycinin, napin, phaseolin, cruciferin, or the like, or genes expressing fatty acid synthesizing enzymes which appear only in the seed. The transcriptional initiation regions may be obtained from any convenient host, particularly, plant hosts such as *Brassica*, e.g. *napus* or *campestris*, soybean (*Glycine max*), beam (*Phaseolus vulgaris*), corn (*Zea mays*), cotton (*Gossypium sp.*), safflower (*Carthamus tinctorius*), tomato (*Lycopersicon esculentum*), and *Cuphea* species. (The disclosure of U.S. Ser. No. 147,781 (filed Jan. 25, 1988) is incorporated by reference in its entirety herein.) Transcriptional initiation regions of particular interest are those associated with the *Brassica napus* or *campestris* napin genes, acyl carrier proteins, gene that express from about 7 to 40 days after anthesis in seed, particularly having maximum expression from about day 10 to about day 20, where the expression is not found in leaves, while the expressed product is found in seed in high abundance.

The transcription initiation region including the regulatory 5' portion will usually be about at least 300 bp, more usually at least about 500 bp, and usually not more than about 2,000 bp. The transcription initiation region will not only include the RNA polymerase binding site and mRNA initiation site, but also the region providing for regulation of transcription. Usually the transcription initiation site will be from a gene endogenous to the plant to be transformed or of the same family, although in many situations this may be found not to be necessary.

The transcription initiation region may be joined to the structural gene including the transit peptide in any convenient manner. Since one need not be concerned about being in reading frame, a convenient site proximal to the initiation codon of the structural gene from which the transcription initiation region is obtained may be employed for linking to the structural gene. The two sequences may be ligated together so as to provide for regulated transcription of the structural gene.

At the 3' terminus of the structural gene will be provided a termination region which is functional in plants. A wide variety of termination regions are available that may be obtained from bacterial genes capable of expression in plant hosts, e.g., bacterial, opine genes, viral genes, and plant genes. The particular termination region is not critical to this invention, there being a number of suitable termination regions described in the literature. However, a seed-specific termination region is preferred, particularly, in conjunction with a seed-specific transcription initiation region.

In preparing the transcription cassette, the various DNA fragments may be manipulated, so as to provide for the DNA sequences in the proper orientation and, as appropriate, in the proper reading frame. Toward this end, adapters or linkers may be employed for joining the DNA fragments or other manipulations may be involved to provide for convenient restriction sites, removal of superfluous DNA, removal of restriction sites, or the like. For this purpose, in vitro mutagenesis, primer repair, restriction, annealing, resection, ligation, or the like may be employed, where insertions, deletions or substitutions, e.g., transitions and transversions, may be involved.

By appropriate manipulations, such as restriction, chewing back or filling in overhangs to provide blunt ends, ligation of linkers, or the like, complementary ends of the fragments can be provided for joining and ligation.

In carrying out the various steps, cloning is employed, so as to amplify the amount of DNA and to allow for analyzing the DNA to ensure that the operations have occurred in a proper manner. A wide variety of cloning vectors are available, where the cloning vector includes a replication system functional in *E. coli* and a marker which allows for selection of the transformed cells. Illustrative vectors include pBR332, pUC series, M13mp series, pACYC184, etc. Thus, the sequence may be inserted into the vector at an appropriate restriction site (s), the resulting plasmid used to transform the *E. coli* host, the *E. coli* grown in an appropriate nutrient medium and the cells harvested and lysed and the plasmid recovered. Analysis may involve sequence analysis, restriction analysis, electrophoresis, or the like. After each manipulation the DNA sequence to be used in the final construct may be restricted and joined to the next sequence, where each of the partial constructs may be cloned in the same or different plasmids.

The artificial construct typically used comprises an expression cassette, which comprises the transcription initiation region, the structural gene having 5' a transit peptide sequence, and a termination region. This construct may be joined to other sequences for a variety of reasons. For example, it is usually desirable to have a means for selecting those cells which contain the construct of interest. In this situation, marker genes are employed which allow for selection of the cells containing the construct, as against untransformed cells. For the most part, the marker involves resistance to biocides, e.g. antibiotics, or complementation of an auxotrophic host. Markers which find use include genes coding for proteins which provide for resistance to antibiotics, such as G418, kanamycin, hygromycin, bleomycin, etc. These markers will usually be joined to transcriptional initiation and termination regions which provide for constitutive expression. Thus, after transformation of the plant cells, one can select for the transformed cells by employing a selective medium which favors transformed-cell proliferation.

By this invention, plant seeds having an increased percentage of medium chain fatty acids can be produced by growing, and harvesting seed produced from a plant having in its genome a heterlogous DNA construct comprising, in the order of transcription: a seed-specific transcription initiation region; in open reading frame a plastid-translocating sequence joined to sequence encoding a protein having thioesterase II activity; and a termination region. By heterologous DNA construct is meant that the construct must contain at least one portion which is not native to the host.

In a preferred embodiment, the seed-specific transcription initiation region is derived from the napin gene of *Brassica napus* and the termination gene is also obtained therefrom. The plastid-translocating sequence comprises an ACP transit sequence and the first 11 amino acids of mature ACP protein. The sequence encoding amino acids having thioesterase II activity is a DNA sequence encoding rteII, missing amino acid residues of the N-terminal end. In other words, upon translocation the protein additive will comprise the C-terminal portion of rteII. In a most preferred embodiment, rteII begins at amino acid residue 8.

Depending upon the manner in which the construct will be introduced into the plant cell, additional sequences may also be necessary. Where the construct is to be introduced by cocultivation of plant cells with *Agrobacterium*, the construct will be joined to at least one T-DNA border, particularly the right border, so that the construct will be joined to a border or be intermediate between the right or left borders. Constructs employing T-DNA borders have found extensive exemplification in the literature, such as in EPA Serial No. 120,516, Hoekema, In: The Binary Plant Vector System Offset-drukkerij Kanters B. V., Alblasserdam, 1985, Chapter V, Fraley, et al., *Crit. Rev. Plant Sci.*, 4:1–46, and An et al., *EMBO J.* (1985) 4:277–284.

Alternatively, to enhance integration into the plant genome, terminal repeats of transposons may be used as borders in conjunction with a transposase. In this situation, expression of the transposase should be inducible, or the transposase inactivated, so that once the transcription construct is integrated into the genome, it should be relatively stably integrated and avoid hopping.

A variety of techniques are available for the introduction of DNA into a plant cell host. These techniques include transformation with Ti-DNA employing *A. tumefaciens* or *A. rhizogenes* as the transforming agent, protoplast fusion, injection, electroporation, etc. For transformation with *Agrobacterium*, plasmids can be prepared in *E. coli* which plasmids contain DNA homologous with the Ti-plasmid, particularly T-DNA. The plasmid may or may not be capable of replication in *Agrobacterium*, that is, it may or may not have a broad spectrum prokaryotic replication system, e.g. RK290, depending in part upon whether the transcription construct is to be integrated into the Ti-plasmid or be retained on an independent plasmid. By means of a helper plasmid, the transcription construct may be transferred to the *A. tumefaciens* and the resulting transformed organism used for transforming plant cells.

Conveniently, explants may be cultivated with the *A. tumefaciens* or *A. rhizogenes* to allow for transfer of the transcription construct to the plant cells, the plant cells dispersed in an appropriate selective medium for selection, grown to callus, shoots grown and plantlets regenerated from the shoots by growing in rooting medium. The *Agrobacterium* host will contain a plasmid having the vir genes necessary for transfer of the T-DNA to the plant cells and may or may not have T-DNA. For injection and electroporation, disarmed Ti-plasmids (lacking the tumor genes, particularly the T-DNA region) may be used to introduce genes into the plant cell.

One or more introns may also be present in the DNA sequences. Also, depending upon the nature of a given DNA sequence, it may be desirable to synthesize the sequence with plant preferred codons. The plant preferred codons may be determined from the codons of highest frequency in the proteins expressed in the largest amount in the particular plant species of interest.

Where electroporation or microinjection is employed, the construct may be introduced into a transposon or be joined to one or both of the long terminal repeats of the transposon plus the transposase, or the transposase may be provided by a helper transposon. In some instances, the construct may be joined to DNA homologous to DNA present in the plant cell nucleus. The particular manner in which the DNA is introduced into the host cell is not critical to this invention so long as a reasonable level of efficiency of transformation is achieved, so that transformed cells may be isolated.

Once the plant cells have been transformed, various techniques are available for regenerating plants from the cells. The cells are introduced into regeneration medium, and, once shoots form, the cells may be transferred to rooting medium to provide for plant growth. The plantlets may then be grown and screened for the expression of the desired gene, using such techniques as Southern, Northern, or Western blots, immunoassays, or the like. These plantlets may then be grown to provide for seeds, which may be analyzed for changes in fatty acid composition.

The cells which have been transformed may be grown into plants in accordance with conventional ways. See, for example, McCormick et al., *Plant Cell Reports* (1986) 5:81–84. These plants may then be grown, and either pollinated with the same transformed strain or different strains, identifying the resulting hybrid having the desired phenotypic characteristic. Two or more generations may be grown to ensure that the subject phenotypic characteristic is stably maintained and inherited in a Mendelian fashion and then seeds harvested to ensure the desired phenotype or other property has been achieved.

Fatty acid compositions of interest will have enhanced amounts of the fatty acids in the 8-16 carbon range, preferably the 8-14 carbon range, particularly having at least 25% by weight of the fatty acids in the range, more particularly having at least about 50% of the fatty acids in this range, usually not having more than about 75% of the fatty acids in that range. Of a particular interest is providing transformed Brassica seed which results in high levels of the low molecular weight (shorter chain) fatty acids.

Thus, plants which are known to provide for high yields of fatty acids in their seeds can be modified in such a way as to become producers of the rarer plant fatty acids, those fatty acids having even number of carbon atoms in the range of 8-14. These modifications can be obtained both in vitro and in vivo, in vitro by adding particular additives to broken chloroplasts or embryo extracts; in vivo by transforming plant cells with appropriate DNA constructs coding for the proteins of interest and having transcription initiation and termination regions subject to cell differentiation regulation.

The following examples are provided by way of illustration and not by way of limitation.

EXPERIMENTAL

EXAMPLE I

Thioesterase II was isolated from the mammary tissue of lactating rats in accordance with the method described by Smith, *Methods in Enzymology* (1981) 71:188-200. Acyl carrier protein is from *E. coli* and is obtained commercially (Sigma Chemical). Acetyl transacylase is isolated from *Brassica napus* R-500.

The isolation of chloroplasts from spinach leaves is described by Jensen and Bassham *Proc. Natl. Acad. Sci. USA* (1966) 56:1095-1101 and involves picking leaves and (1966) :56:1095-1101 and involves picking leaves and immediately placing them in ice water. The midvein is removed and the leaves cut into 0.5 x 0.5cm pieces with a razor blade on an ice-cold glass plate. The pieces are placed in an ice cold semi-micro Waring blender container (Eberback Corporation) and barely covered with chloroplast isolation buffer (25mM MES, pH 6.7, 330mM sorbitol, 2mM EDTA Na$_2$, 1 mM MgCl$_2$ and 1mM MnCl$_2$). After grinding the leaf pieces for 0.5 sec. at low speed, the tissue is held beneath the surface of the buffer with a rubber stopper and ground for 4 sec. at high speed. The ground leaves are then filtered through 3 layers of Miracloth (Calbiochem Biochemicals), which were wetted with water and then allowed to drain. The filtrate is centrifuged at 600xg for 80 sec. (timed after reaching full speed). The supernatant is then decanted, and the pellet is then suspended in 2-4ml isolation buffer with a Pasteur pipette, recentrifuged and then resuspended in about 0.5 ml isolation buffer.

Production of the fatty acid synthesizing system from embryonic plant tissue involves collecting developing seeds, either on the day of production or, if earlier, with freezing in liquid N$_2$ and storing at −80° C. Individual seeds are cut in half, and those with developing embryos present are placed into a buffered medium (50mM MOPS, pH 7.0, 1% soluble polyvinylpyrolidone and 5mM dithiothreitol) until sufficient half seeds have been found. The embryonic tissue is then removed, and the seed coats are discarded. The tissue is typically ground in a minimal amount of the aforementioned buffer using a rotating pestle in a 1.5ml microfuge tube. The pestle is rinsed into the tube and the supernate obtained after centrifugation at 10,000g for 5 min. is used for subsequent fatty acid production.

The fatty acid production employs the procedure described by Ohlrogge, et al., *Proc. Natl. Acad. Sci. USA* (1979) 76:1194-1198. A 4×concentrate of buffer is prepared which is 0.4M TES, pH 7.5, 1.2 mM MgCl$_2$ and 0.8mM MnCl$_2$. NADH reagent is prepared daily by dissolving 1 mg NADH in 100μl buffer concentrate. NADPH reagent is prepared daily by dissolving 1 mg NADPH in 100μl buffer concentrate. ATP reagent contains 50mg/ml ATP and 50mg/ml sodium bicarbonate. A typical reaction mixture of 225μl is constructed by adding 42.6μl 4×buffer concentrate, 7.5μl NADPH reagent, 6.1μl NADH reagent and 2.7μl ATP reagent and 3μl acetyl CoA to provide a final concentration of 4μM. The total volume of 58.9μl is brought to 222μl by addition of water, either chloroplasts (final concentration: 1μg chlorophyll/μl) or embryonic tissue supernate (final concentration: 0.2-1 μg protein/μl), and any additives to be tested for effects on fatty acid composition. The reaction is started by the addition of 3μl of malonyl CoA to the mixture and may be terminated by the addition of the extraction solution, chloroform/methanol.

For fatty acid determination, radiolabelled malonyl-CoA is employed and the following procedure is used.

Fatty acid determination:
I. Extraction
  100μg Fatty Acids (1 μg chlorophyll)/1μl
  Add 175 μl H$_2$O
  Add 500 μl chloroform
  Add 1000 μl methanol
  Add 500 μl 0.88% KCl in H$_2$O
  Centrifuge to separate phases
  Remove lower (green) phase
  Evaporate solvent on ice with N$_2$.
II. Saponification
  Add 180 μl methanol
  Add 65 μl 0.1M KOH in methanol
  Heat 80° C., 20 min
  Evaporate methanol, 80° C. with N$_2$.
III. Derivatization
  Add 150 μl acetonitrile
  Add 50 μl derivatization reagent
    0.1M p-bromophenacyl bromide (BPB)
    5mM 18-crown-6
    (20μg FA/μMol BPB)
  Heat, 80° C., 30 min.
IV. Separation/HPLC
  Make derivatized sample 20% H$_2$O,
  centrifuge 10,000 g, 5 min.
  Inject 100 μl
  C18 column
  Acetonitrile (Acn)/H$_2$O as solvent
  80/20 Acn/H$_2$O as solvent
  At 10 min. →(100/0) over 1 min.
  At 11 min →2ml/min. over 1 min.

In carrying out the fatty acid production rteII was added to give a rate of 1 mmol/min when assayed with decanoyl-CoA, while ACP was added to provide a concentration and reaction mix of about 1.2 pM.

The time for incorporation to obtain the following results was 1 hour. The following table indicates the results.

| Additions | % Incorporation | | |
|---|---|---|---|
| | $C_{14:0}$ | $C_{16:0}$ | $C_{18:0}$ |
| None | — | — | 100.0 |
| ACP | — | 21.3 | 78.7 |
| rteII | — | 12.2 | 87.8 |
| rteII + ACP | 6.4 | 28.4 | 65.2 |

As evidenced from the above results, one can modify a fatty acid profile of fatty acid compositions produced by chloroplasts by introducing one or more proteins involved in a fatty acid synthesis system. In this particular example, ACP has been added back to the mixture to replace ACP lost during the breaking of the chloroplast. If carried out in intact cells, for example, only rteII would need to be provided. rteII is an exogenous material capable of diverting intermediates into the production of lower fatty acids.

EXAMPLE 2

Transport to Plastid: Assay

Construct pCGN1993, comprising a double 35s CaMV promoter, a 1.1 kb ACP-rteII sequence, and a T-DNA transcript 7 termination sequence is electroporated into tobacco leaf protoplast cells according to methods known in the art (Comai, et al. *J. Biol. Chem.* (1988) 263:15104–15109). The cells are incubated for approximately 40 hours and an immuno-precipitated (polyclonal antibody preparation) supernate derived fraction is analyzed by Western blot method for evidence of the imported protein. Uptake activity of the fusion peptide by cell chloroplasts is observed by as shown in FIG. 1.

FIG. 1 shows a band at 30 kd which is the expected molecular weight of the processed fusion peptide encoded by the construct pCGN1993, an unprocessed fusion peptide, 36 kd, is shown in the control lane. The control represents the ACP rteII sequence from pCGN1939 cloned into a riboprotne vector (Promega Corporation, Madison, Wis.), transcribed and the transcripts in vivo translated in a rabbit reticuloycte system, and the translated fusion-protein immuno precipitabled with anti-rteII antibody.

Transit construct pCGN1993 is prepared from plasmids pCGN565, pCGN709 and pCGN1958 as follows. An EcoRI-HindIII fragment of pUC18 (Norrander, et al., Gene (1983) 26:101–106) is inserted into pUC13-Cm (Buckley, K., Ph.D. Thesis, UCSD, CA 1985), creating pCGN565.

pCGN709 is prepared from the Sau3A fragment of pCGN703 containing the 3' region of transcript 7 (corresponding to bases 2396–2920 of pTiA6 (Barker et al., *Plant Mol. Biol.* (1983) 2:325) subcloned into the BamHI site of pUC18. pCGN703 results from the subcloning of the HindIII-BglII fragment of pNW31c-8, 29-1 (Thomashow, et al., Cell (1980) 19:729) containing the open reading frame (ORF) -1 and -2 of pTiA6 into the HindIII-BamHI sites of pCGN566. pCGN566 contains the EcoRI-HindIII linker of pUC18 inserted into the EcoRI-HindIII sites of pUC13-Cm.

The last component pCGN1958 is prepared from the ligation of a 1.3kb BglII-KpnI fragment obtained from pCGN1939 into the 4.6 kb backbone of BamHI, KpnI digested pCGN2113.

Construction of pCGN2113 pCGN2113 contains a double-35S promoter and the tml-3'region with multiple cloning site between them, contained in a pUC-derived plasmid backbone bearing a ampecillen resistance gene; the promoter mcs-3' cassette is bordered by multiple restriction sites for easy removal. pCGN2113 was derived from pCGN986, pCGN164, and pCGN638.

1. Construction of pCGN986. pCGN986 contains a cauliflower mosaic virus 35S (CaMV35) promoter and a T-DNA tml 3'-region with multiple restriction sites between them. pCGN986 was derived from another cassette, pCGN206, containing a CaMV35S promoter and a different 3' region, the CaMV region VI 3'-end. The CaMV 35S promoter was cloned as an AluI fragment (bp 7114–7734) (Gardner et.al., *Nucl. Acids Res.* (1981) 9:2871–2888) into the hincII site of M13mp7 (Messing et. al., Nucl. Acids Res. (1981) 9:309–321) to create C614. An EcoRI digest of C614 produced the EcoRI fragment from C614 containing the 35S promoter which was cloned into the EcoRI site of pUC8 (Viera and Messing, *Gene* (1982) 19:259) to produce pCGN147.

pCGN148a containing a promoter region, selectable marker (KAN with 2 ATG's) and 3' region, was prepared by digesting pCGN528 with BglII and inserting the BamHI-BglII promoter fragment from pCGN147. This fragment was cloned into the BglII site of pCGN528 so that the BglII site was proximal to the kanamycin gene of pCGN528.

The shuttle vector used for this construct, pCGN528, was made as follows: pCGN525 was made by digesting a plasmid containing Tn5 which harbors a kanamycin gene (Jorgenson et. al., *Mol. Gen. Genet.* (1979) 177:65) with HindIII-BamHI and inserting the HindIII-BamHI fragment containing the kanamycin gene into the HindIII-BamHI sites in the tetracycline gene of pACYC184 (Chang and Cohen, *J. Bacteriol.* (1978) 134:1141–1156). pCGN526 was made by inserting the BamHI fragment 19 of pTiA6 (Thomashow et. al., *Cell* (1980) 19:729–739), modified with XhoI linkers inserted into the SmaI site, into the BamHI site of pCGN525. pCGN528 was obtained by deleting the small XhoI fragment from pCGN526 by digesting with XhoI and religating.

pCGN149a was made by cloning the BamHI-kanamycin gene fragment from pMB9KanXXI into the BamHI site of pCGN148a. pMBG9KanXXI is a pUC4K variant (Vieira and Messing, Gene (1982) 19:259–268) which has the XhoI site missing, but contains a functional kanamycin gene from Tn903 to allow for efficient selection in *Agrobacterium*.

pCGN149a was digested with HindIII and BamHI and ligated to pUC8 digested with HindIII and BamHI to produce pCGN169. This removed the Tn903 kanamycin marker. pCGN565 and pCGN169 were both digested with HindIII and Pst1 and ligated to form pCGN203, a plasmid containing the CaMV 35S promoter and part of the 5'-end of the TN5 kanamycin gene (up to the Pst1 site, Jorgenson et al., (1979), supra). A 3'-regulatory region was added to pCGN203 from pCGN204 (an EcoRI fragment of CaMV (bp 408–6105) containing the region VI 3' cloned into pUC18 (Gardner et. al., (1981) supra) by digestion with HindIII and PstI and ligation. The resulting cassette, pCGN206, was the basis for the construction of pCGN986.

The pTiA6 T-DNA tml 3'-sequences were subcloned from the Bam19 T-DNA fragment (Thomashow et al., (1980), supra) as a BamHI-EcoRI fragment (nucleotides 9062 to 12,823, numbering as in Barker et. al., *Plant Mol. Biol.* (1982) 2:335–350) and combined with the pACYC184 (Chang and Cohen (1978), supra) origin of replication as an EcoRI-HindIII fragment and a gentamycin resistance maker (from plasmid pLB41), obtained from D. Figurski) as a BamHI-HindIII fragment to produce pCGN417.

The unique SmaI site of pCGN417 (nucleotide 11,207 of the Bam19 fragment) was changed to a SacI site using linkers and the BamHI-SacI fragment was subcloned into pCGN565 to give pCGN971. The BamHI site of pCGN971 was changed to an EcoRI site using linkers and created pCGN971E. The resulting EcoRI-SacI fragment containing the tml 3' regulatory sequences was joined to pCGN206 by digestion with EcoRI and SacI to give pCGN975. The small part of the Tn5 kanamycin resistance gene was deleted from the 3'-end of the CaMV 35S promoter by digestion with SalI and BglII, blunting the ends and ligation with SalI linkers. The final expression cassetts pCGN986 contains the CaMV 35S promoter followed by two SalI sites, and XbaI site, BamHI, SmaI KpnI and the tml 3' region (nucletodies 11207-9023 of the T-DNA).

2. Construction of pCGN164. The AluI fragment of CaMV (bp 7144-7735) (Gardner et al., *Nucl. Acids Res.* (1981) 9:2871-2888) was obtained by digestion with AluI and cloned in to the HincII site of M13mp7 (Vieira et al., *Gene* (1982) 19:259-) to create C614. An EcoRI digest of C614 produced the EcoRI fragment from C614 containing the 35S promoter which was cloned into the EcoRI site of pUC8 (Vieira et al., (1982) ibid) to produce pCGN146. To trim the promoter region, the BglII site (bp7670) was treated with BglII and Bal31 and subsequently a BglII linker was attached to the Bal31 treated DNA to produce pCGN147. pCGN147 was digested with EcoRI and HphI and the resultant EcoRI-HphI fragment containing the 35S promoter was ligated into EcoRI-SmaI digested M13mp8 to create pCGN164.

3. Construction of pCGN638. Digestion of CaMV10 (Gardner et al., (1981) supra) with BglII produced a BglII fragment containing a 35S promoter region (bp 6493-7670) which was ligated into the BamHI site of pUC19 (Norrander et al., Gene (1983) 26:101-106) to create pCGN638.

4. Construction of pCGN2113. pCGN164 was digested with EcoRV and BamHI to release a EcoRV-BamHI fragment which contained a portion of the 35S promoter (bp 7340-7433); pCGN638 was digested with HindIII and EcoRV to release a HindIII-EcoRV fragment containing a different portion of the 35S promoter (bp 6493-7340). These two fragments were ligated into pCGN986 which had been digested with HindIII and BamHI to remove the HindIII-BamHI fragment containing the 35S-promoter; this ligation produced pCGN639, which contained the backbone and tml-3' region from pCGN986 and the two 35S promoter fragments from pCGN164 and pCGN638. pCGN638 was digested with EcoRV and DdeI to release a fragment of the 35S promoter (bp 7070-7340); the fragment was treated with the Klenow fragment of DNA polymerase I to create blunt ends, and was ligated into the EcoRV site of pCGN639 to produce pCGN2113 having the fragment in the proper orientation.

pCGN1939 includes the transit peptide taken from an ACP cDNA clone of a *B. campestris* seed messenger RNA, the first 11 amino acids that are found on the N-terminal prortion of that mature ACP protein and the rteII sequence (Naggart, et al. (1987) supra) minus the first 7 amino acids. Thus, the first amino acid of the rteII sequence is lysine.

The transit peptide sequence and first 11 amino acids of *B. campestris* ACP cDNA (Rose, et al., (1987) *Nuc. Acids Res.* 15:7197) are cloned into pCGN565. A plasmid containing the EcoRI fragment of the rteII gene is cloned into a pCGN786 backbone creating plasmid 6cl. Together with pUC119, the 6cl and pCGN1Bcs are combined to form construct ddl. ddl is prepared from HindIII-DdeI fragment of IBcs plus a DdeI-BamHI fragment of 6cl inserted into a HindIII and BamHI digested pUC119. pUC119 is prepared from pUC19 (available from Vieira, J. and Messing, J., Waksman Institute, Rutgers University, Rutgers, N.J.) and having the intergenic region of M13, from an HgiAI site at 5465 to the AhaIII site at 5941, being inserted into the NdeI site of the pUC. ddl is then digested with XhoI and SphI for insertion of an XhoI-SphI fragment obtained from 6cl. The result is pCGN1939.

The 0.6kb KpnI-PstI fragment obtained from KpnI and PstI digested pCGN709, and the 3.3kb XbaI-KpnI fragment obtained from XbaI and KpnI digested pCGN1958, are ligated into the XbaI and PstI digested sites of pCGN565 to create pCGN1993.

EXAMPLE 3

Constitutive Plant Expression

The 3.3 kb XbaI fragment of pCGN1993 is inserted into a binary plasmid for transfer of the double 35s-rteII construct into *Agrobacterium*. (The orientation of the XbaI fragment is not critical.)

The resulting plasmid in *E. coli* DH5α (Bethesda Research Laboratories, Gaithensburg, Md.) are conjugated into the *Agrobacterium* strain EHA101 (Hood, et al., *J. Bacteriol.* (1986) 168:1291–1301). The genomic construct is transferred to *Brassica napus* via cocultivation of hypocotyls with the conjugated *Agrobacterium* strain using the techniques similar to those disclosed in W087/07299, which is hereby incorporated by reference. (The protocol of W087/07299 is modified in that the co-cultivation occurs in Murashige-Skoog salt media (K.C. Biologicals), rather than a B5 media, and that the pre-shooting culture period is 3, rather than 7, days.) As discussed in W087/07299, transformed Brassica tissue is selected by kanamycin-resistance and is grown to plant.

EXAMPLE 4

Seed Specific Expression

A seed-specific expression construct is provided having a "long" napin promoter, ACP-rteII sequences from pCGN1939, and a napin derived termination sequence. Preparation of this construct proceeds as follows:

A BglII partial genomic library of *B. campestris* DNA is made in the lambda vector Charon 35 using established protocols (Maniatis et al., (1982). *Molecular Cloning: A Laboratory Manual*, (Cold Spring Harbor Laboratory New York). The titer of the amplified library is $-1.2 \times 10^9$ phage/ml. Four hundred thousand recombinant bacteriophage are plated at a density of $10^5$ per 9×9 in. NZY plate (NZYM as described in Maniatis et al., (1982) supra) in NZY+10 mM MgSO$_4$+0.9% agarose after adsorption to DH1 *E. coli* cells (Hanahan, *Mol. Biol.* (1983) 166:557) for 20 min. at 37° C. Plates are incubated at 37° C. for 13 hours, cooled at 4° C. for 2.5 hours and the phage lifted onto Gene Screen Plus (New England Nuclear) by laying precut filters over the plates for approximately 1 min. and peeling them off. The adsorbed phage DNA is immobilized by floating the filter on 1.5M NaCl, 0.5M NaOH for 1 min., neutralizing in 1.5M NaCl, 0.5 M Tris-HCl, pH 8.0 for 2 min. and 2XSSC for 3 min. Filters are air dried until just damp, prehybridized and hybridized at 42° C. Filters are probed for napin-containing clones using an XhoI-SalI fragment of the cDNA clone BE5 which is isolated from the *B. campestris* seed cDNA library described above using the proble pN1 (Crouch et al., *J. Mol. Appl. Genet.* (1983) 2:273-283). Three plaques which hybridized strongly on duplicate filters were plaque purified as described Maniatis et al., (1982) supra)

One of the clones named lambda CGN1-2 was restriction mapped and the napin gene was localized to overlapping 2.7 kb XhoI and 2.1kb SalI restricting fragments. The two fragments were subcloned from lambda CGN1-2 DNA into pCGN789 (a pUC based vector the same as pUC119 with the normal polylinker replaced by the snythetic linker - 5' GGAATTCGT-CGACAGATCTCTG CAGCTCGAGGGATC-CAAGCTT 3' (which represents the polylinker EcoRI, SalI, BglII, PstI, XhoI, BamHI, HindIII). The identity of the subclones as napin was confirmed by sequencing. The lambda CGN1-2 napin gene is that encoding the mRNA corresponding to the BE5 cDNA as determined by the exact match of their nucleotide sequences.

An expression cassette is constructed from the 5'-end and the 3'-end of the lambda CGN1-2 napin gene. The majority of the napin coding region of pCGN940 is deleted by digestion with SalI and religation to form pCGN1800. Single-stranded dNA from pCGN1800 is used in an in vitro mutagenesis reaction (Adelman et al., DNA (1983) 2:183-193) using the synthetic oligonucleotide 5' GCTTGTTCGCCATGGATATCTTCT-GTATGTTC 3'. This oligonucleotide inserts an EcoRV and an Nco1 restriction site at the junction of the promoter region and the ATG start codon of the napin gene. An appropriate mutant was identified by hybridization to the oligonucleotide used for the mutagenesis and sequence analysis and named pCGN1801.

A 1.7kb promoter fragment was subcloned from pCGN1801 by partial digestion with EcoRV and ligation to pCGN786 (a pCGN556 chloramphenicol based vector with the synthetic linker described above in place of the normal polylinker) cut with EcoRI and blunted by filling in with DNA Polymerase I Klenow fragment to create pCGN1802. 3' sequences from the lambda CGN1-2 napin gene were added to XhoI-HindIII digested pCGN1802 from pCGN941 digested with XhoI and HindIII. The resulting clone, pCGN1803, contains approximately 1.6kb of napin 3'-sequences as well as promoter sequences, but a 326 nucleotide HindIII fragment normally found at the 3'-end of lambda CGN1-2 is inserted opposite to its natural orientation. As a result, there are two HindIII sites in pCGN1803. This reversed fragment was removed by digestion of pCGN1803 with HindIII. Following religation, a clone was selected which now contained only approximately 1.25kb of the original 1.6 napin 3'-sequence. This clone, pCGN1808, is the lambda CGN1-2 expression cassette and contains 1.725kb of napin promoter sequence, and 1.265kb of napin 3' sequences with the unique cloning sites SalI, BglI, PstI, and XhoI in between.

Two restriction sites of pCGN1808 are modified to allow for the insertion of a BglII-KpnI digested pCGN1939 fragment to give ACP-rteII in the expression cassette. First, the 1808 is digested with XhoI and ligated to the annealed, unphosorylated oligonuleotide 5' TCGACGGTACCG 3' to create a KpnI site, and concomitantly eliminate the XhoI site. The resulting construct is further digested with HindIII and ligated to a phosphorylated HindIII-XhoI adapter sequence to create an Xho-I site with concomitant elimination of the HindIII site. After modification of the sites, the construct is digested with BglII and KpnI and ligated to BglII-KpnI digested pCGN1939. This cassette can be digested and ligated to an appropriate binary vector to give an expression binary cassette. The expression binary cassette can be transformed into *Agrobacterium* and co-cultivated with plant tissue, etc., in accordance with the techniques described in Example 3, above.

Upon the incorporation of at least one medium chain fatty acid into any one of the three positions of the triacylglycerol glycerol backbone, a medium chain triacylglycerol is produced. The incorporation of modified fatty acids produced in a plastid into storage lipids by plant cell cytoplasm will produce medium chain triacylglycerols of this invention.

All publications listed in this specification are indicative of the skill and the art to which this invention pertains. Each publication is individually incorporated herein by reference to the same extent and in the same location as if each publication had been individually incorporated by reference.

Although the foregoing invention has been described in some detail by way of illustration and example for purposes of clarify of understanding, it will be obvious that certain changes and modifications may be practiced within the scope of the appended claims.

What is claimed is:

1. A method for changing the fatty acid composition produced by fatty acid synthesizing plastids from a composition having a given proportion of longer chain fatty acids to a composition having a lower proportion of longer chain fatty acids, comprising:

combining the fatty-acid-producing components from isolated broken plastids with a fatty-acid-composition-modifying amount of thioesterase II in the presence of metabolites in the fatty acid pathway, said metabolites being malonyl-CoA and either acetyl-CoA or a metabolite subsequent in the metabolic pathway to malonyl-CoA.

2. The method of claim 1, wherein said plastids are chloroplasts.

3. The method of claim 3, wherein said chloroplasts are spinach chloroplasts.

4. The method of claim 1, wherein said fatty-acid-producing components comprise a broken entire chloroplast.

5. The method of claim 1, wherein said longer chain fatty acids have 18 or more carbon atoms.

6. The method of claim 1, wherein said thioesterase II is a mammalian protein.

7. A method for changing the fatty acid composition produced by fatty acid synthesizing plastids from a composition having a given proportion of medium chain fatty acids to a composition having a higher proportion of medium chain fatty acids, comprising:

combining the fatty-acid-producing components from isolated broken plastids with a fatty-acid-composition-modifying amount of thioesterase II in the presence of metabolites in the fatty acid pathway, said metabolites being malonyl-CoA and either acetyl-CoA or a metabolite subsequent in the metabolic pathway to malonyl-CoA.

8. The method of claim 7, wherein said medium chain fatty acids contain 14 or fewer carbon atoms.

9. The method of claim 7, wherein said plastids are chloroplasts.

* * * * *